(12) United States Patent
Haeselhoff et al.

(10) Patent No.: US 8,853,431 B2
(45) Date of Patent: Oct. 7, 2014

(54) PROCESS FOR THE PREPARATION OF 17-(3-HYDROXYPROPYL)-17-HYDROXY STEROIDS

(75) Inventors: Claus Christian Haeselhoff, Gladbeck (DE); Mike Petersen, Hamm (DE)

(73) Assignee: Bayer Intellectual Property GmbH, Monheim (DE)

( * ) Notice: Subject to any disclaimer, the term of this patent is extended or adjusted under 35 U.S.C. 154(b) by 1805 days.

(21) Appl. No.: 12/147,828

(22) Filed: Jun. 27, 2008

(65) Prior Publication Data
US 2009/0012286 A1    Jan. 8, 2009

Related U.S. Application Data

(60) Provisional application No. 60/946,762, filed on Jun. 28, 2007.

(30) Foreign Application Priority Data

Jun. 28, 2007  (DE) .......................... 10 2007 030 596

(51) Int. Cl.
C07J 71/00    (2006.01)
C07J 53/00    (2006.01)
C07J 9/00     (2006.01)

(52) U.S. Cl.
CPC .................................. *C07J 53/008* (2013.01)
USPC .............................. 552/513; 552/553; 540/23

(58) Field of Classification Search
USPC .................................... 540/23; 552/513, 553
See application file for complete search history.

(56) References Cited

U.S. PATENT DOCUMENTS

| | | | | | |
|---|---|---|---|---|---|
| 4,303,741 | A | * | 12/1981 | Klein ............................. | 428/611 |
| 4,435,327 | A | * | 3/1984 | Petzoldt et al. ............... | 552/615 |
| 4,614,616 | A | * | 9/1986 | Petzoldt et al. ................ | 540/4 |
| 5,106,995 | A | * | 4/1992 | Plotkin ........................ | 549/273 |
| 6,121,465 | A | * | 9/2000 | Mohr et al. ................... | 549/265 |
| 6,933,395 | B1 | * | 8/2005 | Mohr et al. ................... | 549/265 |
| 7,319,154 | B2 | * | 1/2008 | Seilz et al. .................... | 549/265 |
| 7,585,971 | B2 | * | 9/2009 | Costantino et al. ............ | 540/15 |

FOREIGN PATENT DOCUMENTS

| | | | |
|---|---|---|---|
| DE | 10 2007 030 596 B3 | | 3/2009 |
| EP | 0 075 189 | | 3/1983 |
| EP | 0 075 189 | A1 | 3/1983 |
| EP | 0 918 891 | | 6/1999 |
| WO | WO-98 04764 | | 2/1998 |
| WO | WO 01/58919 | * | 8/2001 |
| WO | WO-2007 009821 | | 1/2007 |

OTHER PUBLICATIONS

Gui-Dong Zhu and Okamura, Synthesis of Vitamin D (Chemical Reviews, 1996, vol. 95, No. 6, 1877-1952).*

International Search Report of PCT/EP2008/058296 (Mar. 3, 2009).
K. M. Sam et al., "Steroidal Spiro-γ-Lactones That Inhibit 17β-Hydroxysteroid Dehydrogenase Activity in Human Placental Microsomes", J. Med. Chem., vol. 38 (1995) pp. 4518-4528.

* cited by examiner

*Primary Examiner* — Sabiha N Qazi
(74) *Attorney, Agent, or Firm* — Millen, White, Zelano & Branigan, P.C.

(57) ABSTRACT

The present invention relates to a process for the preparation of 17α-(3-hydroxypropyl)-17β-hydroxysteroids of the formula I

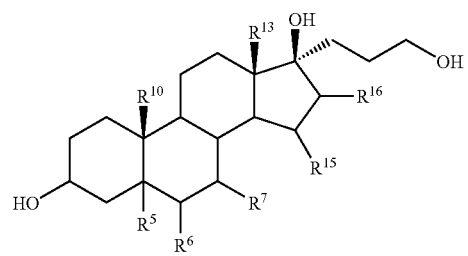

starting from 17-ketosteroids of the formula III

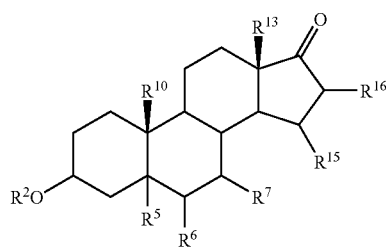

via the intermediates of the formula V

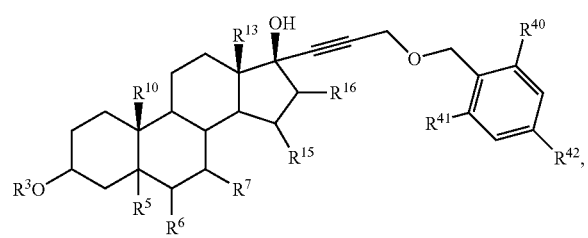

wherein the radicals $R^3$, $R^5$, $R^6$, $R^7$, $R^{10}$, $R^{13}$, $R^{15}$, $R^{16}$, $R^{40}$, $R^{41}$ and $R^{42}$ have the meaning indicated in the description.

11 Claims, No Drawings

PROCESS FOR THE PREPARATION OF 17-(3-HYDROXYPROPYL)-17-HYDROXY STEROIDS

This application claims the benefit of the filing date of U.S. Provisional Application Ser. No. 60/946,762 filed Jun. 28, 2007.

The present invention relates to a process for the preparation of 17α-(3-hydroxypropyl)-17β-hydroxysteroids, the intermediates of the process as such, a process for their preparation and the use of the intermediates for the preparation of steroid 21,17-spirolactones, in particular drospirenone.

17α-(3-Hydroxypropyl)-17β-hydroxysteroids of the formula I

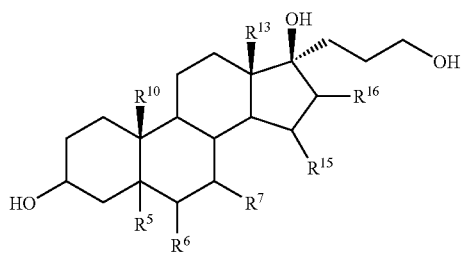

I serve as starting substances for the synthesis of pharmacologically active steroid 21,17-carbolactones, such as, for example, of eplerenone (9α,11α-epoxy-7α-methoxycarbonyl-3-oxo-17α-pregn-4-ene-21,17-carbolactone), drospirenone (6β,7β;15β,16β-dimethylene-3-oxo-17-pregn-4-ene-21,17-carbolactone, spironolactone (7α-acetylthio-3-oxo-17α-pregn-4-ene-21,17-carbolactone, canrenone (3-oxo-17α-pregna-4,6-diene-21,17-carbolactone) and prorenone (6β,7β-methylene-3-oxo-17α-pregn-4-ene-21,17-carbolactone).

The synthesis of such steroid 21,17-spirolactones is carried out by the oxidation of the corresponding 17α-(3-hydroxypropyl)-17β-hydroxysteroids

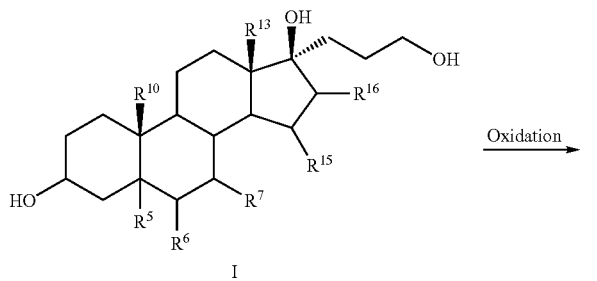

I

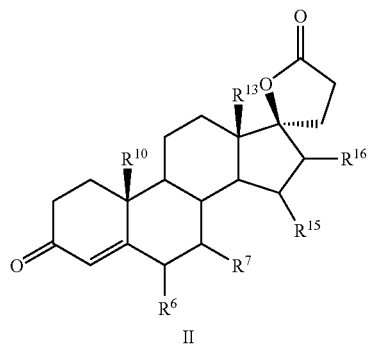

II using suitable oxidants such as chromic acid (Sam et al. J. Med. Chem. 1995, 38, 4518-4528), pyridinium chlorochromate (EP 075189), pyridinium dichromate (Bittler et al; Angew. Chem. 1982, 94, 718-719; Nickisch et al. Liebigs Ann. Chem. 1988, 579-584), potassium bromate in the presence of a ruthenium catalyst (EP 918791) or with an alkali metal or alkaline earth metal hypochlorite in the presence of a TEMPO catalyst (WO 2007/009821); and optionally after acid-catalysed elimination of water.

17-(3-Hydroxypropyl)-17-hydroxysteroids can be prepared by the hydrogenation of 17-(3-hydroxy-1-propynyl)-17-hydroxysteroids. The synthesis of the 17-(3-hydroxy-1-propynyl)-17-hydroxysteroids is carried out by the base-induced addition of prop-1-yn-3-ol to the corresponding 17-ketosteroids [Bittler et al.; Angew. Chem. 1982, 94, 718-719; Nickisch et al.; J. Med. Chem. 1987, 30, 1403-1409; EP 075189 B1].

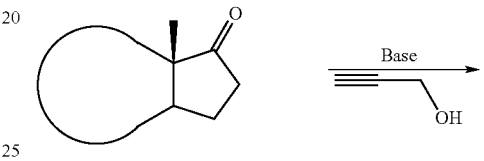

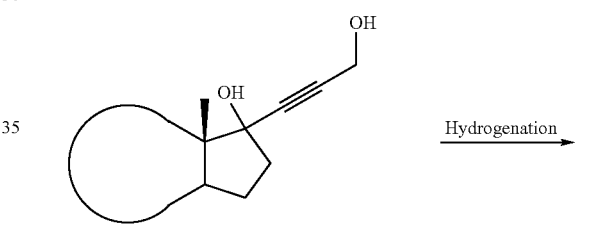

A disadvantage in the use of prop-1-yn-3-ol (propargyl alcohol) as a functionalized C3 structural unit is the distinctly pronounced byproduct formation (in particular 17-ethynyl steroids) caused by its instability to bases.

The instability of propargyl alcohol all in all leads to an obstacle to the isolation of the pure product and to a decrease in the yield.

The object of the present invention therefore consists in making available an alternative process for the preparation of 17α-(3-hydroxypropyl)-17β-hydroxysteroids of the formula I from the corresponding 17-ketosteroids of the formula III, which makes it possible to prepare the target compounds in higher yield and purity.

This object has been achieved according to the invention by a process for the preparation of 17α-(3-hydroxypropyl)-17β-hydroxysteroids of the formula I,

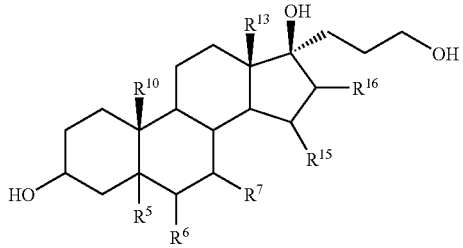

which comprises the following steps:
a) reaction of 17-ketosteroids of the formula III

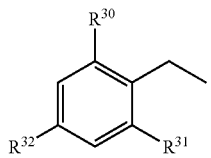

wherein
$R^3$ can be hydrogen or the group

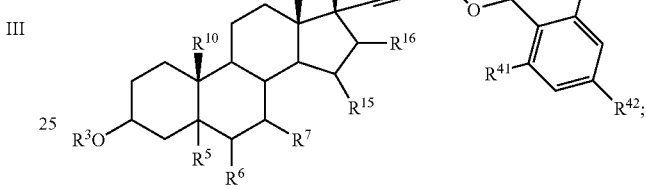

wherein
$R^{30}$, $R^{31}$, $R^{32}$ independently of one another can be hydrogen, $C_1$-$C_4$-alkyl or $C_1$-$C_4$-alkoxy;
$R^5$ can be hydrogen, hydroxyl or together with $R^6$ can be a double bond;
$R^6$ can be hydrogen, together with $R^5$ or $R^7$ can be a double bond; or together with $R^7$ can be an α or β-$CH_2$ group;
$R^7$ can be hydrogen, $C_1$-$C_4$-alkyl, $C_1$-$C_4$-alkoxycarbonyl, $C_1$-$C_4$-thioacyl; together with $R^6$ can be a double bond or an α or β-$CH_2$ group;
$R^{10}$ can be hydrogen, methyl or ethyl;
$R^{13}$ can be methyl, ethyl;
$R^{15}$ can be hydrogen, $C_1$-$C_4$-alkyl, or together with $R^{16}$ can be a —$CH_2$ group or a double bond;
$R^{16}$ can be hydrogen or together with $R^{15}$ can be a —$CH_2$ group or a double bond,
in the presence of a base, with a prop-1-yn-3-ol ether of the formula IV

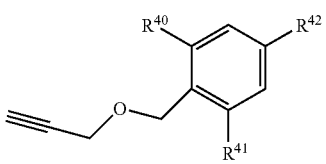

wherein
$R^{40}$, $R^{41}$, $R^{42}$ independently of one another can be hydrogen, $C_1$-$C_4$-alkyl or $C_1$-$C_4$-alkoxy;
to give compounds of the general formula V

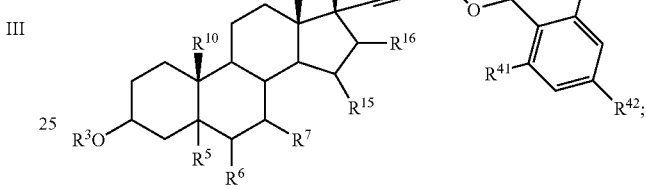

b) complete catalytic hydrogenation of the alkyne function of the compound V, and
c) removal of the benzylic protective group.

Suitable bases for the addition of the propynol ether (step a) are alkali metal or alkaline earth metal alkoxides. Alkali metal methoxides, ethoxides and tert-butoxides are preferred. Potassium tert-butoxide (KOtBu) in THF as a solvent has proven particularly suitable. The addition is preferably carried out in a temperature range from 0° C. to 50° C.

For the purpose of complete hydrogenation of the alkyne function, the compounds of the formula V are reacted with hydrogen as a solution or suspension according to known methods in the presence of a transition metal catalyst [V. Jäger and H. G. Viehe in "Methoden der organischen Chemie" [Methods of Organic Chemistry] (Houben-Weyl), Volume V/2a, pp. 693-700]. The hydrogenation product can subsequently be debenzylated with hydrogen, without isolation or purification being necessary, either in the presence of, for example, Pd/carbon [Larcheveque et al., Tetrahedron; 1988, 44, 6407-6418] or else by Birch reduction [Itoh et al., Tetrahedron Lett.; 1986; 27, 5405-5408] to give the compounds of the formula I.

The catalyst used for the hydrogenation of the alkyne function is preferably Raney nickel or palladium on various carrier materials.

The catalytic debenzylation is carried out in the presence of suitable transition metal hydrogenation catalysts, preferably Pd/carbon or Pd(OH)$_2$/carbon. Particularly suitable solvents for this step are protic solvents such as, for example, ethanol.

Alternatively to hydrogenating debenzylation, the removal of the benzyl group can also be carried out by Birch reduction. For this, the hydrogenation product is reacted in an inert solvent mixture with alkali metals (lithium, sodium, potassium) or alkaline earth metals (calcium). Preferably, the solvent used is a mixture of liquid $NH_3$ or a primary amine and an ethereal solvent (tetrahydrofuran, diethyl ether, dimethoxyethane, diglyme etc). Lithium or sodium is preferred as a reductant. According to the invention, the Birch reduction is very preferably carried out with lithium in a solvent mixture of liquid $NH_3$ and dimethoxyethane.

The yield of compounds of the formula I from the Birch reduction is comparable with that from catalytic debenzylation.

The present invention further also relates to the compounds of the formula V as intermediates and to the process for their preparation, namely a process for the preparation of compounds of the formula V

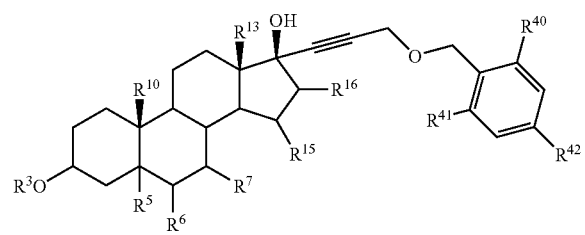

comprising the following step
a) reaction of 17-ketosteroids of the formula III

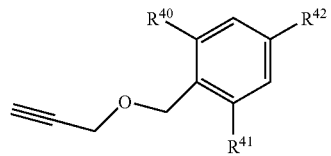

wherein
$R^3$ can be hydrogen or the group

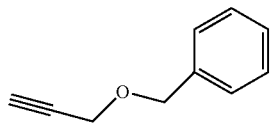

wherein
$R^{30}$, $R^{31}$, $R^{32}$ independently of one another can be hydrogen, $C_1$-$C_4$-alkyl or $C_1$-$C_4$-alkoxy;
$R^5$ can be hydrogen, hydroxyl or together with $R^6$ can be a double bond;
$R^6$ can be hydrogen, together with $R^5$ or $R^7$ can be a double bond; or together with $R^7$ can be an α or β-$CH_2$ group;
$R^7$ can be hydrogen, $C_1$-$C_4$-alkyl, $C_1$-$C_4$-alkoxycarbonyl, $C_1$-$C_4$-thioacyl; together with $R^6$ can be a double bond or an α or β-$CH_2$ group;
$R^{10}$ can be hydrogen, methyl or ethyl;
$R^{13}$ can be methyl, ethyl;
$R^{15}$ can be hydrogen, $C_1$-$C_4$-alkyl, or together with $R^1$ can be a —$CH_2$ group or a double bond;
$R^{16}$ can be hydrogen or together with $R^{15}$ can be a —$CH_2$ group or a double bond,
in the presence of a base, with a prop-1-yn-3-ol ether of the formula IV

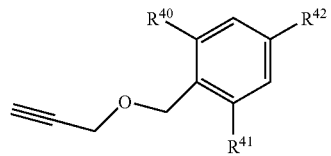

wherein
$R^{40}$, $R^{41}$, $R^{42}$ independently of one another can be hydrogen, $C_1$-$C_4$-alkyl or $C_1$-$C_4$-alkoxy.

According to the present invention, the process in which 17-ketosteroids of the formula III are reacted with a prop-1-yn-3-ol ether of the formula IV wherein $R^{40}$, $R^{41}$, $R^{42}$ independently of one another are hydrogen, namely with the prop-1-yn-3-ol-benzyl ether IVa

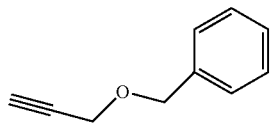

is preferred.

The process according to the invention for the preparation of the compounds of the formula I is particularly suitable and therefore preferred in which process compounds of the formula III,
wherein
$R^5$ is hydrogen or hydroxyl;
$R^6$ is hydrogen or together with $R^7$ is an α or β-$CH_2$ group;
$R^7$ is hydrogen or an α or β-$CH_2$ group;
$R^{10}$ is hydrogen, methyl or ethyl;
$R^{13}$ is methyl, ethyl;
$R^{15}$ is hydrogen, $C_1$-$C_4$-alkyl, or together with $R^{16}$ is a —$CH_2$ group;
$R^{16}$ is hydrogen or together with $R^{15}$ is a —$CH_2$ group,
are employed.

A particularly preferred process according to the present invention is the process for the preparation of the compound Ia,

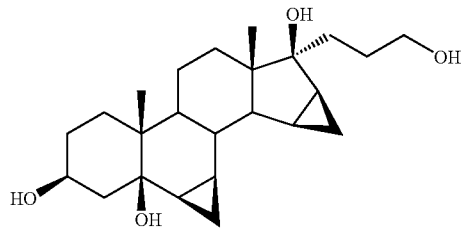

in which in step a) compound IIIa

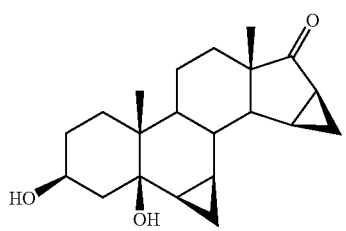

IIIa is reacted to give Va

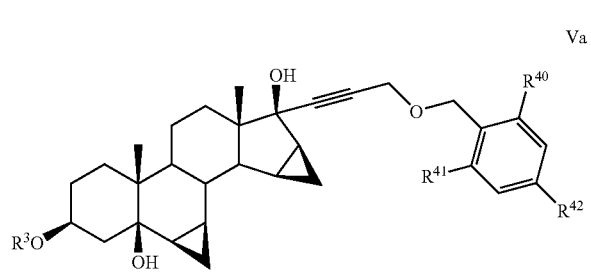

Va and is reacted further in the steps b) and c).

A very particularly preferred process according to the present invention is the process for the preparation of the compound Ia,

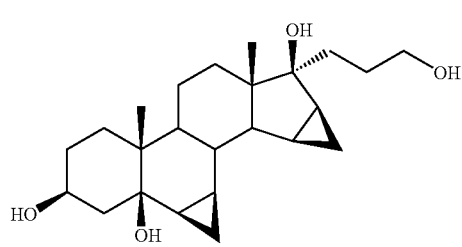

Ia in which in step a) the compound IIIa

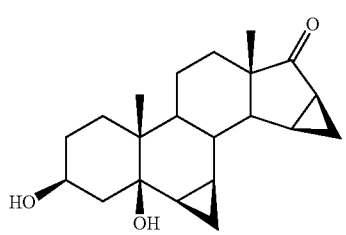

IIIa is reacted in the presence of a base, with the prop-1-yn-3-ol ether of the formula IVa

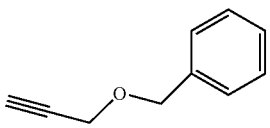

IVa to give the compound Vb

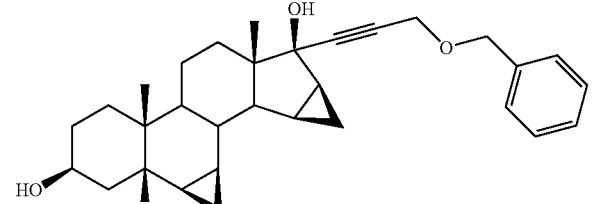

Vb and is reacted further in the steps b) and c) to give the compound Ia.

TABLE 1

Comparison of the yields of the process according to the invention compared to processes of the prior art

| Process/reagent in step a) | Yield (% of theory) | | |
|---|---|---|---|
| | IIIa → Vb | Vb → Ia | Total (IIIa → Ia) |
| process according to the invention/IVa | 92 | 99 | 91 |
| EP 75189/prop-1-yn-3-ol | 75* | 99 | 74 |

*the 17α-(3-hydroxyl-1-propynyl) derivative

Compound Ia is obtained in high purity with a total yield of 91% of theory and can be reacted without further purification according to known methods to give compound IIa (drospirenone) [EP 075189 B1, EP 918791 B1, WO 2007/009821].

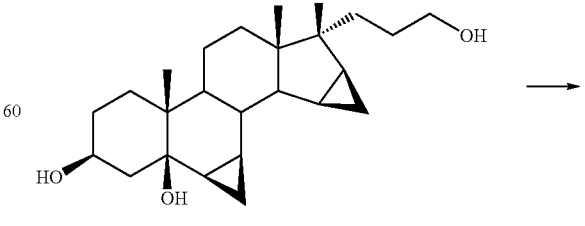

Ia

-continued

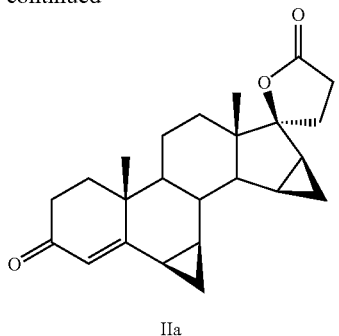

IIa

Reference is made explicitly here to Example H on p. 5, l. 25-32 in EP 075189B1; the examples of p. 5, l. 56-58 to p. 6, l. 1-22 in EP 0918791 B1 and the examples on pp. 12-15 and the entire disclosure content in WO 2007/009821. The processes for the reaction of the compound Ib to give drospirenone (compound IIa) described therein belong to the disclosure content of the present patent application.

By the use of the intermediates Va or Vb for the preparation of drospirenone, the total yield of drospirenone is increased by at least 15%. The high purity of the intermediate Ia obtained in the process according to the invention leads to further process advantages (no intermediate isolation).

Preparation Processes

General Working Procedure 1 (GWP1): Synthesis of Compounds of the Formula V 606.1 mmol of an alkali metal or alkaline earth metal alkoxide, preferably potassium tert-butoxide, are dissolved in 120 ml of tetrahydrofuran. A solution or suspension of 121.2 mmol of a compound of the formula I or II and 133.3 mmol of a propynol ether of the formula III in 520 ml of tetrahydrofuran is metered into the mixture at −20 to 50° C., preferably at 0 to 5° C. After reaction is complete, the reaction mixture is treated with 280 ml of water and subsequently rendered neutral by addition of acid, preferably acetic acid. The aqueous phase is separated off and discarded.

The crude products obtained after evaporation of tetrahydrofuran are recrystallized from a suitable solvent and dried.

EXAMPLE 1

6β,7β;15β,16β-Dimethylene-17-(3-benzyloxypropynyl)androstane-3β,5β,17β-triol (Vb)

According to GWP1, 100 g (0.303 mol) of 3β,5β-dihydroxy-6β,7β;15β,16β-dimethyleneandrostan-17-one were reacted with 48.7 g (0.333 mol) of prop-1-yn-3-ol benzyl ether.

The crude product was recrystallized from 700 ml of toluene. 133 g (0.279 mol) of 6β,7β;15β,16β-dimethylene-17α-(3-benzyloxypropynyl)androstane-3β,5β,11β-triol=92% of theory were obtained.

$[\alpha]_D^{20}$=−70.1° (CHCl$_3$, 12.15 mg in 1 ml of solution, T=20° C., d=100 mm).

$^1$H-NMR (400 MHz, CDCl$_3$): δ=0.37-0.42 (1H, m, H-30 exo*), 0.63 (1H, td, J=9.0 Hz and 5.1 Hz, H-31 endo), 0.78 (1H q, J=5.1 Hz, H-31 endo), 0.82-0.88 (1H, m, H-6), 0.85 (3H, s, H-19), 0.91 (3H, s, H-18), 1.13 (1H, tt, J=8.4 Hz and 4.3 Hz, H-7), 1.15-1.27 (4H, m, H-30 exo, H-1, H-9, H-11), 1.39-1.44 (1H, m, H-2α), 1.46-1.54 (3H, m, H-11, H-12β, H-15), 1.57 (1H, dt, J=13.6 Hz and 2.9 Hz, H-2β), 1.66-1.74 (3H, m, H-12α, H-16, H-8), 1.84 (1H, td, J=14.5 Hz and 2.9 Hz, H-1β), 1.96-2.01 (1H, m, H-4β), 2.04 (1H, dd, J=12.1 Hz and 3.7 Hz, H-1), 2.23 (1H, dd, J=15.0 Hz and 3.3 Hz, H-4α), 2.15-2.35, 2.55-2.70, 3.25-3.50 (3H, strongly broadened, 3 times OH), 4.03 (1H, s, br., H-3), 4.30 (2H, s, H-22), 4.64 (2H, s, H-23), 7.29-7.38 (5H, m, H-25, H-26, H-27, H-28, H-29)

$^{13}$C-NMR (400 MHz, CDCl$_3$): δ=8.97 (CH$_2$, C-30), 11.69 (CH$_2$, C-31), 15.20 (CH, C-7), 16.67 (CH, C-15), 18.26 (CH$_3$, C-18), 19.04 (CH$_3$, C-19), 21.79 (CH$_2$, C-11), 25.34 (CH, C-6), 26.81 (CH$_2$, C-1), 27.06 (CH, C-16), 27.69 (CH$_2$, C-2), 34.20 (CH, C-8), 38.62 (CH$_2$, C-12), 40.42 (C, C-10), 42.65 (C, C-13), 43.04 (CH$_2$, C-4), 44.59 (CH, C-9), 52.88 (CH, C-14), 57.63 (CH$_2$, C-22), 67.09 (CH, C-3), 71.59 (CH$_2$, C-23), 74.84 (C, C-5), 79.80 (C, C-17), 82.06 (C, C-21), 88.99 (C, C-20), 127.93 (CH, C-27), 128.06 (CH, C-26, C-28), 128.44 (CH, C-25, C-29), 137.40 (C, C-24)

MS (CI): m/e=476 (M+NH$_4$−H$_2$O)$^+$, 459 (M+H−H$_2$O)$^+$, 441 (459−H$_2$O), 348 (M+NH$_4$−C$_{10}$H$_{10}$O)$^+$, 331 (476−C$_{10}$H$_9$O), 313 (331−H$_2$O), 295 (313−H$_2$O), 164 (C$_{11}$H$_{16}$O$^+$), 91 (C$_7$H$_7^+$)

IR: ν=3390 (O—H, stretching oscillation of alcohols), 3088, 3018 (C—H, stretching oscillation of aromatic and olefinic hydrocarbon), 2937, 2867 (C—H, stretching oscillation of aliphatic hydrocarbon), 2225 (C≡C, stretching oscillation of alkyne), 1052 (C—O, stretching oscillation of alcohols), 739 (=C—H, deformation oscillation of aromatic or olefinic hydrocarbon)

EXAMPLE 2

15β,16β-Methylene-17α-(3-benzyloxypropynyl)androst-6-ene-3β,5β,17β-triol

According to GWP1, 100 g (0.317 mol) of 3β,5β-dihydroxy-15β,16β-methylene-androst-6-en-17-one were reacted with 50.9 g (0.349 mol) of prop-1-yn-3-ol benzyl ether.

The crude product was recrystallized from 700 ml of toluene. 134.5 g (0.291 mol) of 15β,16β-methylene-17α-(3-benzyloxypropynyl)androst-6-ene-5β,17β-diol=92% of theory were obtained.

$[\alpha]_D^{20}$=−120.3° (CHCl$_3$, 12.15 mg in 1 ml of solution, T=20° C., d=100 mm)

$^1$H-NMR (400 MHz, CDCl$_3$): δ=0.35-0.42 (1H, m, H-30 exo), 0.95 (3H, s, H-18), 0.96 (3H, s, H-19), 1.14 (1H, ddd J=6.8 Hz, 3.7 Hz and 3.5 Hz, H-30 endo*), 1.28-1.35 (1H, m, H-11β), 1.38-1.42 (1H, m, H-15), 1.45-1.51 (2H, m, H-1β, H-2), 1.50-1.60 (3H, m, H-12β, H-11α, H-9), 1.60-1.65 (1H, m, H-2), 1.67-1.73 (2H, m, H-16, H-12α), 1.83-1.89 (1H, m, H-1α), 1.88-1.97 (3H, m, both H-4, H-14), 2.15-2.19 (1H, m, H-8), 2.25-2.40, 2.90-3.10, 3.05-3.25 (3H, strongly broadened, 3 times OH), 4.04-4.07 (1H, m, H-3), 4.28 (2H, s, H-22), 4.62 (2H, s, H-23), 5.49 (1H, dd J=10.0 Hz and 2.8 Hz, H-6), 5.68 (1H, dd J=10.0 Hz and 1.8 Hz, H-7), 7.29-7.36 (5H, m, H-25, H-26, H-27, H-28, H-29)

$^{13}$C-NMR (400 MHz, CDCl$_3$): δ=8.90 (CH$_2$, C-30), 16.25 (CH, C-15), 18.05 (CH$_3$, C-19), 18.28 (CH$_3$, C-18), 21.12 (CH$_2$, C-11), 24.73 (CH$_2$, C-1), 27.31 (CH, C-16), 27.89 (CH$_2$, C-2), 36.53 (CH, C-8), 38.77 (CH$_2$, C-12), 39.12 (C, C-10), 40.68 (CH$_2$, C-4), 42.86 (C, C-13), 43.99 (CH, C-9), 51.27 (CH, C-14), 57.59 (CH$_2$, C-22), 67.31 (CH, C-3), 71.56 (CH$_2$, C-23), 75.93 (C, C-5), 79.71 (C, C-17), 82.13 (C, C-21), 88.88 (C, C-20), 127.93 (CH, C-27), 128.02 (CH, C-7), 128.05 (CH, C-26, C-28), 128.44 (CH, C-25, C-29), 134.52 (CH, C-6), 137.35 (C, C-24)

MS (CI): m/e=480 (M+NH$_4$)$^+$, 462 (480–H$_2$O), 445 (M+H)$^+$, 427 (445–H$_2$O), 334 (480–C$_{10}$H$_{10}$O), 317 (462–C$_{10}$H$_9$O), 299 (317–H$_2$O), 281 (299–H$_2$O), 244 (C$_{17}$H$_{24}$O$^+$), 164 (C$_1$H$_{16}$O$^+$), 91 (C$_7$H$_7^+$)

IR: ν=3480, 3425 cm$^{-1}$ (O—H); 3119, 3025 cm$^{-1}$ (C—H, stretching oscillation of aromatic and olefinic hydrocarbon); 2950 cm$^{-1}$ (C—H, stretching oscillation of aliphatic hydrocarbon); 2225 cm$^{-1}$ (C≡C, stretching oscillation of alkyne); 1055 cm$^{-1}$ (C—O, stretching oscillation of alcohols).

General Working Procedure 2 (GWP2): Hydrogenation and Birch Reduction of the Compounds of the Formula V to Compounds of the Formula I 277 mmol of a compound of the formula V are dissolved in 924 ml of dimethoxyethane and treated with 1.7% by weight of Pd/C (10%). The mixture is first reacted with hydrogen at 20° C. and a pressure of 3 bar. After absorption of hydrogen is complete, the reaction mixture is warmed to 50° C. and stirred until the end of gas absorption. The catalyst is removed by filtration. The filtrate is metered at −40° C. into a solution prepared from 396 ml of dimethoxyethane, 699 ml of NH$_3$ and at least 1664 mmol of lithium. Subsequently, 406 ml of methanol are added in portions. After warming the reaction mixture to 20° C., the latter is added to a solution of 76 ml of acetic acid in 1320 ml of water and the mixture is neutralized by addition of further acetic acid and then freed of dimethoxyethane and methanol by vacuum distillation. The precipitated solid is isolated, washed with water and dried at 50° C.

General Working Procedure 3 (GWP3): Hydrogenation and Hydrogenating Debenzylation of the Compounds of the Formula V to Compounds of the Formula I The filtrate prepared according to GWP2 is freed completely of solvent by distillation. The distillation residue is taken up in 660 ml of ethanol and 2% by weight of Pd(OH)$_2$/C (15-20%) are added. The mixture is reacted with hydrogen at 20° C. and a pressure of 3 bar. After absorption of hydrogen is complete, the catalyst is separated off by filtration. After addition of 660 ml of water, ethanol is removed by distillation. The precipitated solid is isolated, washed with water and dried at 50° C.

EXAMPLE 3

6β,7β;15β,16β-Dimethylene-17-(3-hydroxypropyl)androstane-3β,5β,17β-triol (Ia)

100 g (0.210 mol) of 6β,7β;15β,16β-dimethylene-17-(3-benzyloxypropynyl)androstane-3β,5β,17β-triol were reacted according to GWP2 or GWP3. 81.1 g (0.208 mol) of 6β,7β;15β,16β-dimethylene-17-(3-hydroxypropyl)androstane-3β,5β,17β-triol=99% of theory were obtained.

MS (CI): m/e=389 (M–H)$^+$, 373 (M+H–H$_2$O)$^+$, 355 (373–H$_2$O), 337 (355–H$_2$O), 319 (337–H$_2$O).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2007 030 596.8, filed Jun. 28, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula V

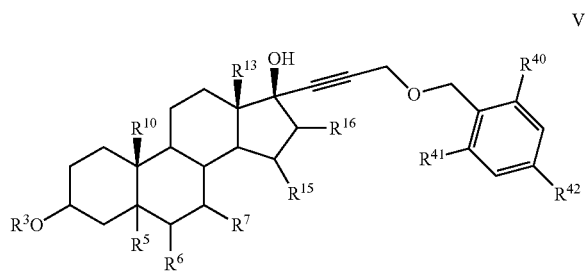

wherein
R$^3$ is hydrogen or

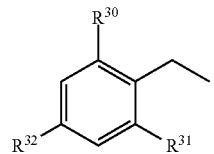

R$^{30}$, R$^{31}$, R$^{32}$ are, independently of one another, hydrogen, C$_1$-C$_4$-alkyl or C$_1$-C$_4$-alkoxy;
R$^5$ is hydrogen, or hydroxyl or together with R$^6$ can be a double bond;
R$^6$ is hydrogen, or together with R$^5$ or R$^7$ is a double bond; or together with R$^7$ is an α or β-CH$_2$ group;
R$^7$ is hydrogen, C$_1$-C$_4$-alkyl, C$_1$-C$_4$-alkoxycarbonyl, C$_1$-C$_4$-thioacyl; or together with R$^6$ is a double bond or an α or β-CH$_2$ group;
R$^{10}$ is hydrogen, methyl or ethyl;
R$^{13}$ is methyl, or ethyl;
R$^{15}$ is hydrogen, or C$_1$-C$_4$-alkyl, or together with R$^{16}$ is a —CH$_2$ group or a double bond;
R$^{16}$ is hydrogen or together with R$^{15}$ is a —CH$_2$ group or a double bond, and
R$^{40}$, R$^{41}$, R$^{42}$ independently of one another is hydrogen, C$_1$-C$_4$-alkyl or C$_1$-C$_4$-alkoxy.

2. A compound according to claim 1, which is a compound of formula Va

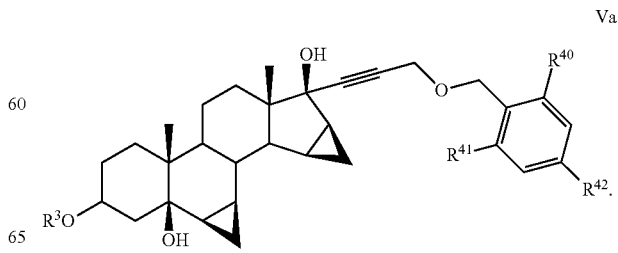

3. A compound according to claim 1, which is a compound of formula Vb

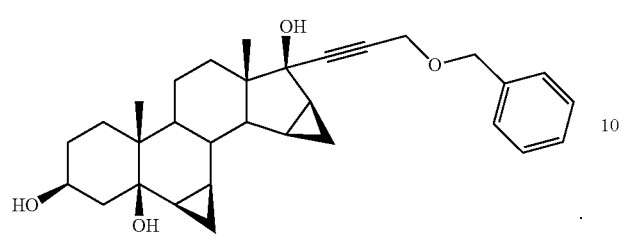

4. A compound according to claim 1, which is 6β,7β;15β,16β-dimethylene-17α-(3-benzyloxypropynyl)androstane-3β,5β,17β-triol.

5. 1A process in which a reaction of a compound of formula V according to claim 1 leads to the preparation of a 17α-(3-hydroxypropyl)-17β-hydroxysteroid of formula I

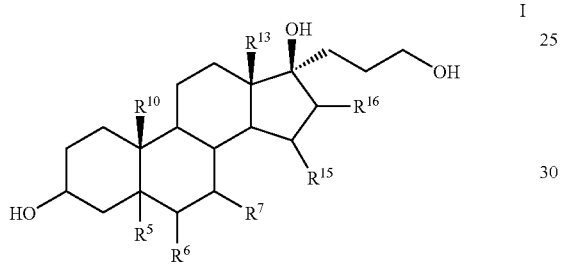

comprising
a) reacting a 17-ketosteroid of formula III

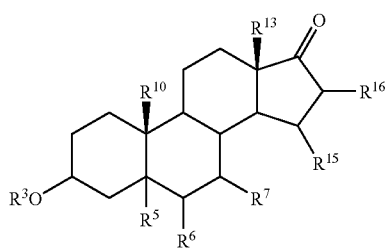

wherein
$R^3$ is hydrogen or the group

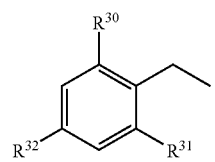

$R^{30}$, $R^{31}$, $R^{32}$ are, independently of one another, hydrogen, $C_1$-$C_4$-alkyl or $C_1$-$C_4$-alkoxy;
$R^5$ is hydrogen, or hydroxyl or together with $R^6$ is a double bond;
$R^6$ is hydrogen, or together with $R^5$ or $R^7$ is a double bond; or together with $R^7$ is an α or β-$CH_2$ group;

$R^7$ is hydrogen, $C_1$-$C_4$-alkyl, $C_1$-$C_4$-alkoxycarbonyl, $C_1$-$C_4$-thioacyl; or together with $R^6$ is a double bond or an α or β-$CH_2$ group;
$R^{10}$ is hydrogen, methyl or ethyl;
$R^{13}$ is methyl, or ethyl;
$R^{15}$ is hydrogen, or $C_1$-$C_4$-alkyl, or together with $R^{16}$ is a —$CH_2$ group or a double bond; and
$R^{16}$ is hydrogen or together with $R^{15}$ is a —$CH_2$ group or a double bond,
in the presence of a base,
with a prop-1-yn-3-ol ether of formula IV

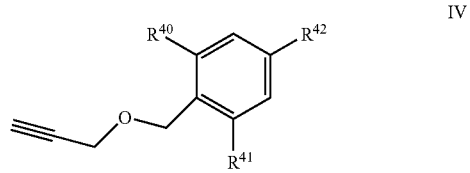

wherein
$R^{40}$, $R^{41}$, $R^{42}$ are, independently of one another, hydrogen, $C_1$-$C_4$-alkyl or $C_1$-$C_4$-alkoxy,
to give a compound of formula V

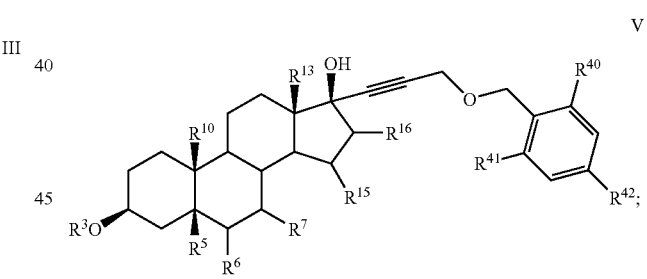

b) completely catalytic hydrogenating the alkyne function of the compound of formula V,
and
c) removing the benzylic protective group.

6. A process according to claim 5, wherein in the compound of formula III
$R^5$ is hydrogen or hydroxyl;
$R^6$ is hydrogen or together with $R^7$ is an α or β-$CH_2$ group;
$R^7$ is hydrogen or an α or β-$CH_2$ group;
$R^{10}$ is hydrogen, methyl or ethyl;
$R^{13}$ is methyl, or ethyl;
$R^{15}$ is hydrogen, or $C_1$-$C_4$-alkyl, or together with $R^{16}$ is a —$CH_2$ group; and
$R^{16}$ is hydrogen or together with $R^{15}$ is a —$CH_2$ group.

7. A process according to claim 5, wherein the compound of formula I is a compound of formula Ia

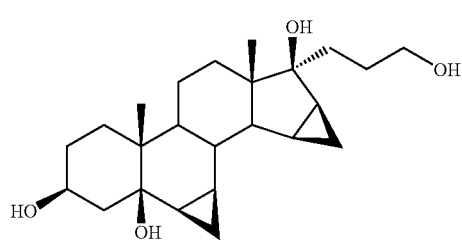

Ia wherein the compound of formula III is a compound of formula IIIa

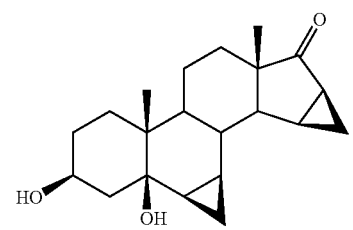

IIIa and wherein the compound of formula V is a compound of formula Va

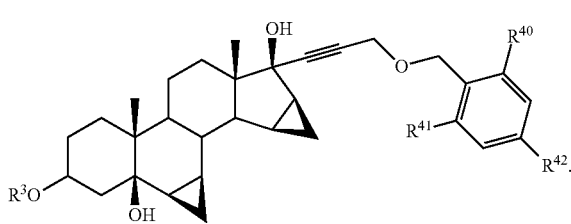

Va

8. A process according to claim 5, wherein the prop-1-yn-3-ol ether is a compound of formula IVa

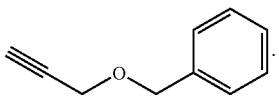

IVa

9. A process according to claim 5, wherein the compound of formula I is a compound of formula Ia

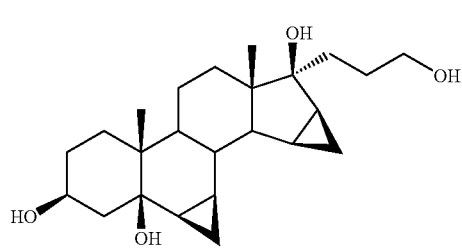

Ia wherein the compound of formula III is a compound of formula IIIa

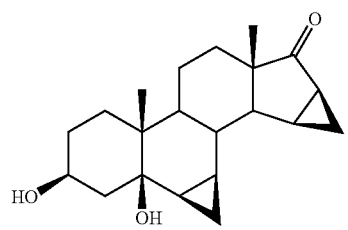

IIIa wherein the compound of formula IV is a compound of formula IVa

IVa and wherein the compound of formula V is a compound of formula Vb

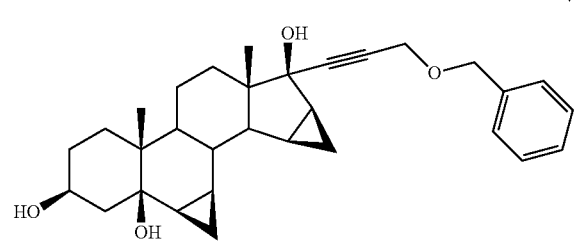

Vb

10. A process for preparing a compound of formula V

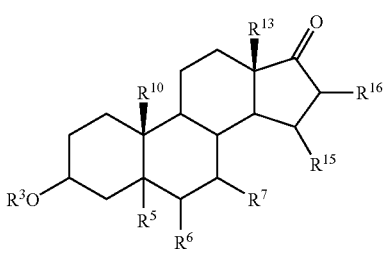

V comprising
reacting a 17-ketosteroid of formula III

III wherein
R³ is hydrogen or the group

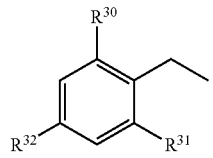

R³⁰, R³¹, R³² are, independently of one another, hydrogen, $C_1$-$C_4$-alkyl or $C_1$-$C_4$-alkoxy;
R⁵ is hydrogen, or hydroxyl or together with R⁶ is a double bond;
R⁶ is hydrogen, or together with R⁵ or R⁷ is a double bond; or together with R⁷ is an α or β-$CH_2$ group;
R⁷ is hydrogen, $C_1$-$C_4$-alkyl, $C_1$-$C_4$-alkoxycarbonyl, $C_1$-$C_4$-thioacyl; or together with R⁶ is a double bond or an α or β-$CH_2$ group;
R¹⁰ is hydrogen, methyl or ethyl;
R¹³ is methyl, or ethyl;
R¹⁵ is hydrogen, or $C_1$-$C_4$-alkyl, or together with R¹⁶ is a —$CH_2$ group or a double bond; and
R¹⁶ is hydrogen or together with R¹⁵ is a —$CH_2$ group or a double bond, in the presence of a base,
with a prop-1-yn-3-ol ether of formula IV

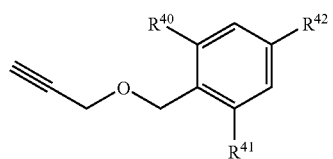

wherein
R⁴⁰, R⁴¹, R⁴² are, independently of one another, hydrogen, $C_1$-$C_4$-alkyl or $C_1$-$C_4$-alkoxy.

11. A process according to claim 10, wherein the prop-1-yn-3-ol ether is a compound of formula IVa

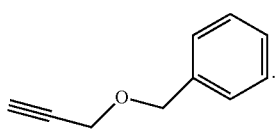

* * * * *